(12) United States Patent
Kirchhofer (10) Patent No.: US 7,727,201 B2
(45) Date of Patent: Jun. 1, 2010

(54) DOSING DEVICE WITH PRIMING FUNCTION

(75) Inventor: Fritz Kirchhofer, Sumiswald (CH)

(73) Assignee: TecPharma Licensing AG, Burgdorf (CH)

(*) Notice: Subject to any disclaimer, the term of this patent is extended or adjusted under 35 U.S.C. 154(b) by 959 days.

(21) Appl. No.: 11/119,359

(22) Filed: Apr. 29, 2005

(65) Prior Publication Data

US 2006/0258989 A1 Nov. 16, 2006

(51) Int. Cl.
*A61M 5/00* (2006.01)

(52) U.S. Cl. .................. 604/208; 604/68; 604/72; 604/131; 604/151; 604/154; 604/181; 604/187; 604/207; 604/209; 604/210; 604/211; 604/224; 604/227; 604/228

(58) Field of Classification Search .............. 604/68, 604/72, 131, 151, 154, 181, 207–210, 224, 604/227, 228
See application file for complete search history.

(56) References Cited

U.S. PATENT DOCUMENTS

| 2,695,023 | A | * | 11/1954 | Brown | 604/210 |
|---|---|---|---|---|---|
| 3,882,849 | A | * | 5/1975 | Jamshidi | 604/210 |
| 4,466,426 | A | * | 8/1984 | Blackman | 604/187 |
| 4,973,318 | A | * | 11/1990 | Holm et al. | 604/208 |
| 5,318,544 | A | * | 6/1994 | Drypen et al. | 604/210 |
| 5,514,097 | A | * | 5/1996 | Knauer | 604/136 |
| 5,755,686 | A | * | 5/1998 | O'Neill et al. | 604/508 |
| 5,807,346 | A | | 9/1998 | Frezza et al. | |
| 5,938,642 | A | * | 8/1999 | Burroughs et al. | 604/208 |
| 6,241,709 | B1 | | 6/2001 | Bechtold et al. | |
| 6,485,470 | B2 | * | 11/2002 | Hostettler et al. | 604/208 |
| 6,824,024 | B2 | * | 11/2004 | Ingenhoven et al. | 222/504 |
| 2004/0097883 | A1 | * | 5/2004 | Roe | 604/207 |

FOREIGN PATENT DOCUMENTS

| DE | 19900827 C1 | 8/2000 |
|---|---|---|
| DE | 10047637 A1 | 4/2002 |
| WO | WO 9607443 A1 * | 3/1996 |
| WO | WO 03/020347 A2 | 3/2003 |
| WO | WO 2004/064902 A | 8/2004 |

\* cited by examiner

*Primary Examiner*—Nicholas D Lucchesi
*Assistant Examiner*—Scott Medway
(74) *Attorney, Agent, or Firm*—Dorsey & Whitney LLP; David E. Bruhn (57) ABSTRACT

A device for the dosed administration of an injectable product, including a housing with a receptacle for the product and a drive mechanism movable via a dosing element supported displaceably in the housing, wherein the drive mechanism includes engagement elements situated together in groups, the distance between the groups corresponding to a dosing amount of the injectable product and the distance between the engagement elements corresponding to a priming amount of the injectable product, and wherein the dosing element is coupled to the drive mechanism so that the dosing element at one time interacts with a group of engagement elements to administer the dosing amount and at another time interacts with an engagement element to release the priming amount.

19 Claims, 5 Drawing Sheets

Dosed

Fig. 5b

Primed

Fig. 5c

Neutral

DOSING DEVICE WITH PRIMING FUNCTION

BACKGROUND

The present invention relates to devices and methods for administering or dispensing selected amounts of substances, including devices and methods used in medicine. More particularly, it relates to devices and methods for delivering a selected amount or dose of a substance, including dosing devices that provide for a semi-automated priming function, and to the dosed administration of an injectable product.

Devices for the dosed administration or delivery of a medication, such as insulin, hormones, and the like, are well known. Such devices include injection devices, including those known as injection pens. An injection pen is an injection device that a patient, for example a diabetic, can operate in order to self-administer a desired dose of insulin. Typically, such injection pens possess a dosing knob that projects from an opening of a housing. For the administration of an injection, the dose to be administered is selected or set by means of the dosing knob. Through the turning of the dosing knob, a drive means is preset. For the injecting, the dosing knob is then moved forward from a first end position slightly into the housing, until a second end position is reached. In the process, the preset amount of the product to be injected is administered. Further, in the process of injecting a drive means is moved forward and acts on a piston, which acts on the injectable product in an ampoule, so that the medication is displaced from the ampoule and expelled or delivered via a cannula.

After administration of the medication, it is typically necessary to prepare the injection pen for a new, subsequent injection by carrying out a priming process. As is known, in this process the cross-section or central bore of the injection cannula is deaerated as well as freed of residual materials through the expelling of a certain small amount of the product to be injected without an injection being carried out.

This priming process, which may be referred to more simply as priming, is an additional operating step for a patient that has to undertake an injection, which step must not be forgotten if an optimal injection after the priming is to be obtained. In at least one known dosing device or injection pen, a priming is effected in that, through the rotating of an adjusting section, a changeover from an administration position into a priming position is achieved. This adjustment must be reset again for a subsequent administration or injection. This requires an additional effort and additional attention of the patient. It is precisely in stressful situations, when a quick insulin injection must absolutely take place, that the patient can inadvertently disregard or improperly carry out this operating process.

SUMMARY

Accordingly, an object of the present invention to propose an injection and/or dosing device that makes possible an alternative manner of accomplishing a priming function. Further, it is an object of the invention to make available a simplified priming function that can be advantageously integrated into existing mechanical components of dosing devices.

In one embodiment, the present invention comprises a device for the dosed administration of an injectable product, the device comprising a housing with a receptacle for the product and a drive mechanism movable via a dosing element supported displaceably in the housing, wherein the drive mechanism comprises engagement elements situated together in groups, the distance between the groups corresponding to a dosing amount of the injectable product and the distance between the engagement elements corresponding to a priming amount of the injectable product, and wherein the dosing element is coupled to the drive mechanism so that the dosing element at one time interacts with a group of engagement elements to administer the dosing amount and at another time interacts with an engagement element to release the priming amount. The present invention encompasses a method of using an injection or dosing device comprising the step of priming the device.

In one embodiment, the present invention comprises a device for the dosed administration of an injectable product, including a housing with a receptacle for the product, a conveying means is provided for a predetermined dose, and a drive means is provided for the conveying means, wherein the drive means is movable via a dosing element supported displaceably in the housing, wherein according to the invention the drive means displays engagement elements that are situated together in groups, wherein a dosing distance between the groups corresponds to a dosing amount and a priming distance between the engagement elements corresponds to a priming amount of the injectable product; and wherein the dosing element is coupled to the drive means in such a way that the dosing element one time interacts with a group of engagement elements and another time with an engagement element, in order to administer a dosing amount of the injectable product the one time and to release the priming amount the other time.

In one embodiment, the present invention comprises a dosing device wherein a section or portion of the device for the dosing is coupled to a priming apparatus. In particular, a means is provided with engagement elements that are situated together in groups, wherein a dosing distance between the groups corresponds to a dosing amount and a priming distance between the engagement elements corresponds to a priming amount.

In addition, according to a preferred embodiment, a dosing knob can be connected to the drive means in such a way that the dosing knob or the dosing element, as the case may be, interacts one time with a group of engagement elements and another time with an individual engagement element, in order to administer the dose amount the one time and to dispense the priming amount the other time. In this design according to the invention, the drive means for the dosed administration also includes, in an integrated and immediate manner, the capability of controlling the priming function. In this way, it can be ensured that a priming function precedes each administration function, and respectively follows the latter. In addition, a first priming function, after a new ampoule has been installed, can be managed in this manner.

Of course, instead of a dosing knob a different suitable dosing element can be used, as long as the patient can transfer a force that ultimately leads to a dosed administration or delivery. Therefore, the term "dosing knob" should be thought of as exemplifying any suitable dosing or dose setting element or structure.

Advantageously, an advancing sleeve is provided, which is connected to the dosing knob. The advancing sleeve acts on the drive means in order to transfer a propulsion force from the dosing knob to the drive means. Thus, with the advancing sleeve a transfer element is provided whereby a propulsion force exerted by the patient can be transferred, via the dosing knob and the advancing sleeve, to the drive means in order to act upon a piston that expels the injectable product from the ampoule or other reservoir or receptacle present in the dosing device.

Advantageously, a group of engagement elements includes at least two engagement elements. The distance between two successive groups of engagement elements is utilized in order to make possible a maximum shift, i.e., to administer a defined, predetermined dose.

The distance between two successive engagement elements of a group can be dimensioned or selected in such a way that this distance corresponds precisely to the priming amount that is to be expelled in order to perform the priming function.

Should a person operating the dosing device according to the present invention want to perform an injection or administration, the person would pull on the dosing knob, whereby the knob moves the advancing sleeve axially in a direction opposite to the expelling direction, i.e., away from the injection needle. The advancing sleeve is moved by a dosing distance, so that an engagement catch on a section of the advancing sleeve that is forcipate at least in cross section, can come into engagement with an engagement element of a following group of engagement elements of the drive means. Subsequently, the patient would be able to move the dosing knob in the expelling direction of the injection needle, whereby the dosing knob moves the advancing sleeve axially forward and in doing so advances the drive means, for example a threaded rod, toothed rod, or the like. The drive means acts on the piston and causes the expelling of a predetermined amount of injectable product, for example insulin. Subsequently, in order to prepare the next injection, the patient can pull again on the dosing knob, whereby the catch on the advancing sleeve then becomes disengaged from the engagement element of the group and is moved to a following engagement element of the same group. Should the patient pull the dosing knob completely out, beyond the distance that corresponds to a dosing distance, then the catch on the advancing sleeve would slide across the drive means, over a distance over which no engagement element is provided, and the catch on the advancing sleeve could not come into engagement with the engagement elements of the following group because the additionally necessary distance to be bridged cannot be traveled by the advancing sleeve due to the limited distance that the dosing knob can travel. With a subsequent actuation of the dosing knob, the advancing sleeve is again advanced without being able to come into engagement with an engagement element. Only when the catch of the advancing sleeve has come into engagement with the last engagement element of the preceding group can the drive means be again advanced and, corresponding to the short distance between the engagement elements of a group, is merely a priming amount of injectable product expelled.

After this process is concluded, the patient can then pull the dosing knob backward again, whereby the catch on the advancing sleeve again becomes disengaged from the last engagement element, and glides over the drive means so long as no engagement element of a following group is present in order to, when the dosing knob has been pulled out the maximum possible distance, come into engagement with an engagement element of a following group. This maximum distance then corresponds again to a maximum propulsion movement, which in principle is capable of releasing a maximum possible dose. Accordingly, a group of engagement elements should display at least two engagement elements, wherein the distance between the two engagement elements of a group should correspond to the priming amount and the distance between two groups should correspond to a maximum dose. Dosing amounts deviating from a maximum dose can be otherwise set, for example by means of a settable propulsion path for the drive means and/or the advancing sleeve. That is to say, while the dosing knob in connection with the advancing sleeve can be pulled back always the same distance, the drive means or the advancing sleeve, as the case may be, can be advanced by an adjustable path, in order to be able to administer different amounts of the injectable product.

In some embodiments, a group of engagement elements is advantageously characterized by the fact that there is a greater distance between groups of engagement elements than between the engagement elements of a group. This should generally be true because a priming amount is generally smaller than a dosed or injected amount.

In order to further ease the operation for the patient, a dosing device according to the present invention can be provided with a priming indicator. This will give a signal indicating that an actuation of the drive means and/or the dosing knob has brought about a priming-function readiness. In this way, the patient need not recall the current operational state of the device, which further enhances the functional reliability.

In some embodiments, an injection or dosing device in accordance with the present invention may comprise a guide apparatus, for example a guide sleeve, that is likewise capable of coming into engagement with the engagement elements of the drive means in order to be able to hold the drive means in a position, while the advancing apparatus is pulled by means of the dosing knob. Via the engagement position of the guide apparatus and that of the advancing sleeve, i.e., the distance between these, a variable dosing can be effected. Here, a stop on the advancing sleeve would have to be appropriately set, so that although the dosing knob can be always pulled back over the same distance, the drive motion is adjustably limited, matching the spacing of the engagement positions.

According to one embodiment of the present invention, the drive means displays equal distances between at least some of the groups of engagement elements. By means of these equal distances between the groups, it is possible to fixedly set an individual dose amount of an injectable product. The dosing device according to the present invention is also used as an expendable pen, i.e., in this case no additional ampoule need be present, but it is also possible to accommodate the product without a replaceable ampoule directly in a receptacle of the housing.

In some preferred embodiments, the drive means is formed between the groups in a smooth manner, that is to say, between the groups the drive means displays no engagement elements or structures belonging to the groups.

BRIEF DESCRIPTION OF THE DRAWINGS

FIG. 5, including FIGS. 5a to 5c, shows a section through the device according to FIG. 1 in the region of the priming indicator, in different positions.

DETAILED DESCRIPTION

Figure 1:
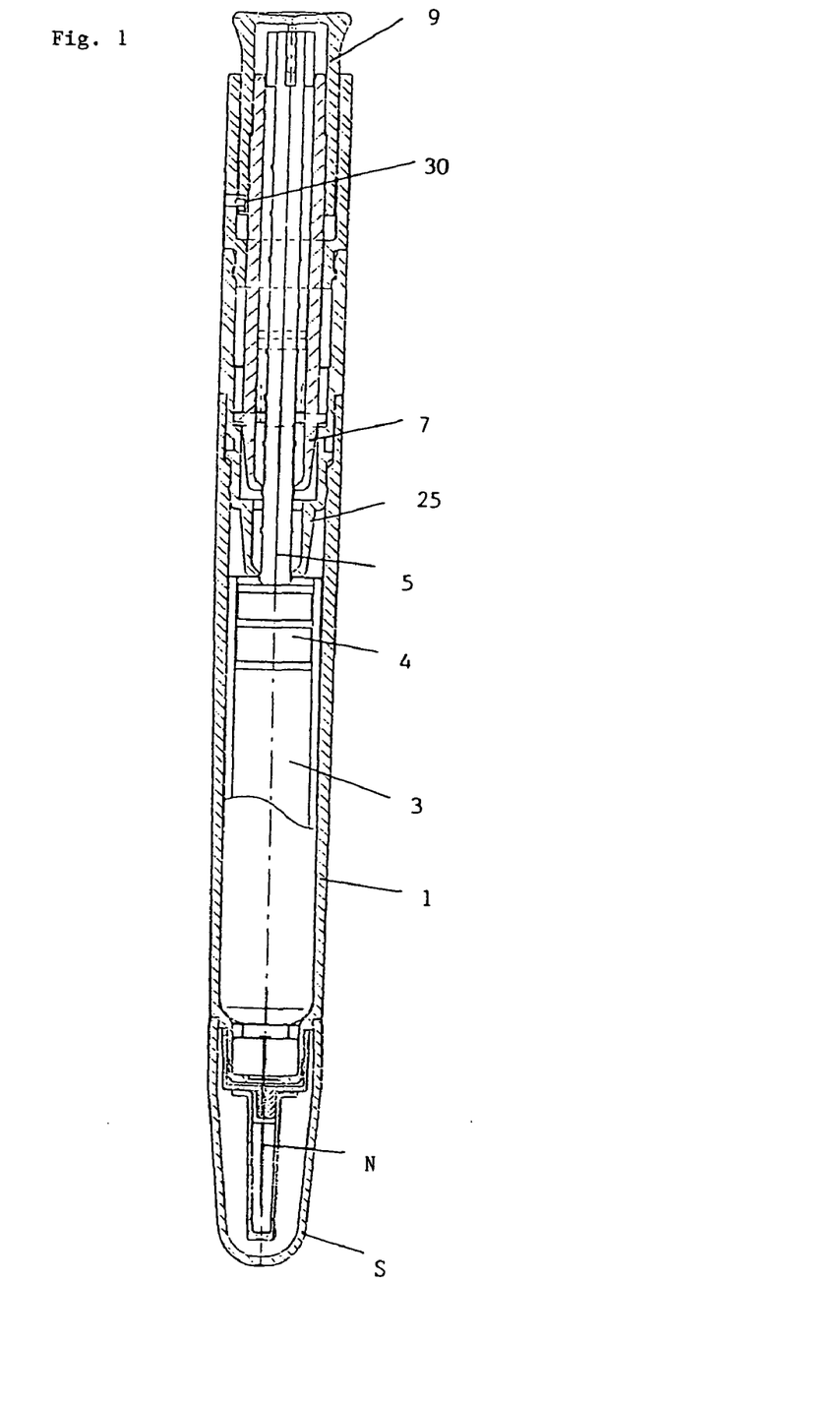
FIG. 1 is an axial, longitudinal section through a device in accordance with the present invention.

Represented in FIG. 1 is one embodiment of a device in accordance with the present invention, the device having a housing 1 with an end (which may be referred to as the front end) carrying an injection needle or cannula N, which is enclosed by a protective cap S. A further jacketing for the injection needle N can be provided, but this is generally removed upon initial use and, for reasons of sterility, arranged only with the attachment or mounting of a new injection needle N.

Provided further in the housing 1 is an ampoule 3 that is equipped with a piston 4 that is moveable inside the ampoule in order to be able to expel an injectable product. In the axial direction of the cylindrical housing 1, a drive means 5, for example a toothed rod, a threaded rod, or the like, is attached to the piston 4. The drive means is moved within a guide apparatus, in particular a guide sleeve 25, and within an advancing apparatus, in particular an advancing sleeve 7, in an axial direction forward in the direction of the injection needle N or backward in the direction of a dosing knob 9.

The dosing knob 9 is fixed to the advancing apparatus or advancing sleeve 7, as the case may be. The dosing knob 9 displays an indicator 30 that is intended to indicate when a priming function can be carried out.

The components of the dosing device according to the invention are further described below with reference to FIGS. 2 to 5. It should be noted that in the figures identical reference numerals are used for the same or functionally similar components, so that a repeated description of the same components is unnecessary.

Figure 2:
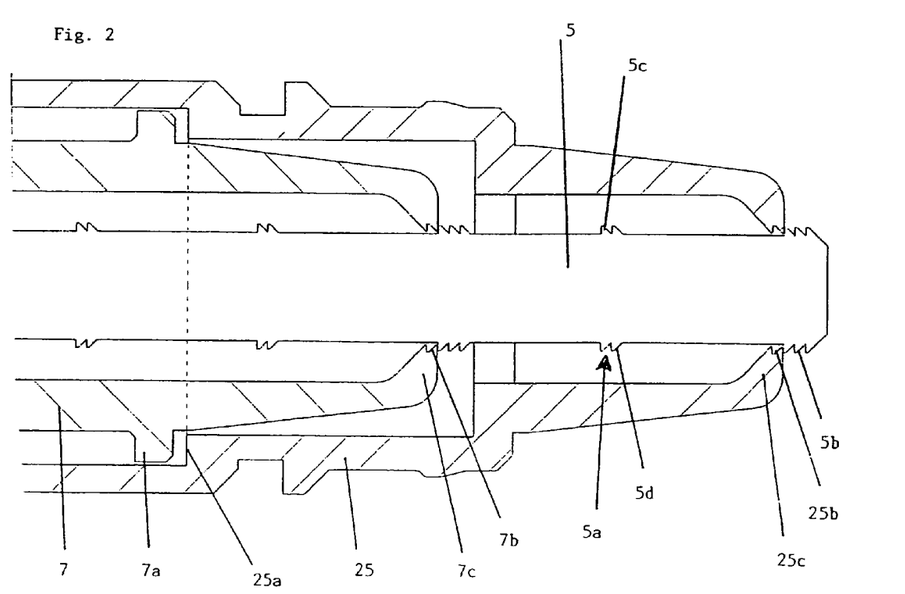
FIG. 2 is an axial, longitudinal section through a drive region, modified according to the invention, of the device of FIG. 1 in an administration position.
Figure 3:
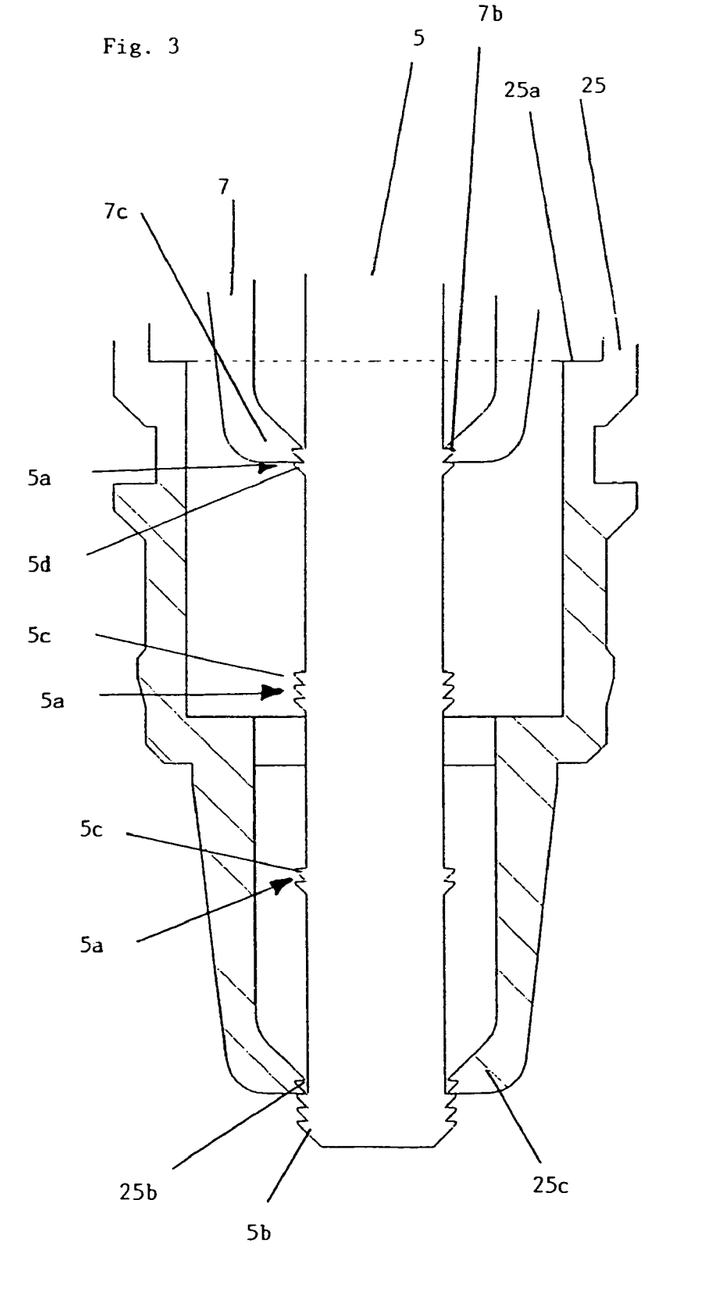
FIG. 3 is a representation corresponding to FIG. 2, wherein a priming function is carried out.

In FIG. 2, the drive means, comprising a toothed rod 5, the advancing sleeve 7, and the guide sleeve 25, are reproduced in a general manner in a cross-sectional view.

Figure 4:
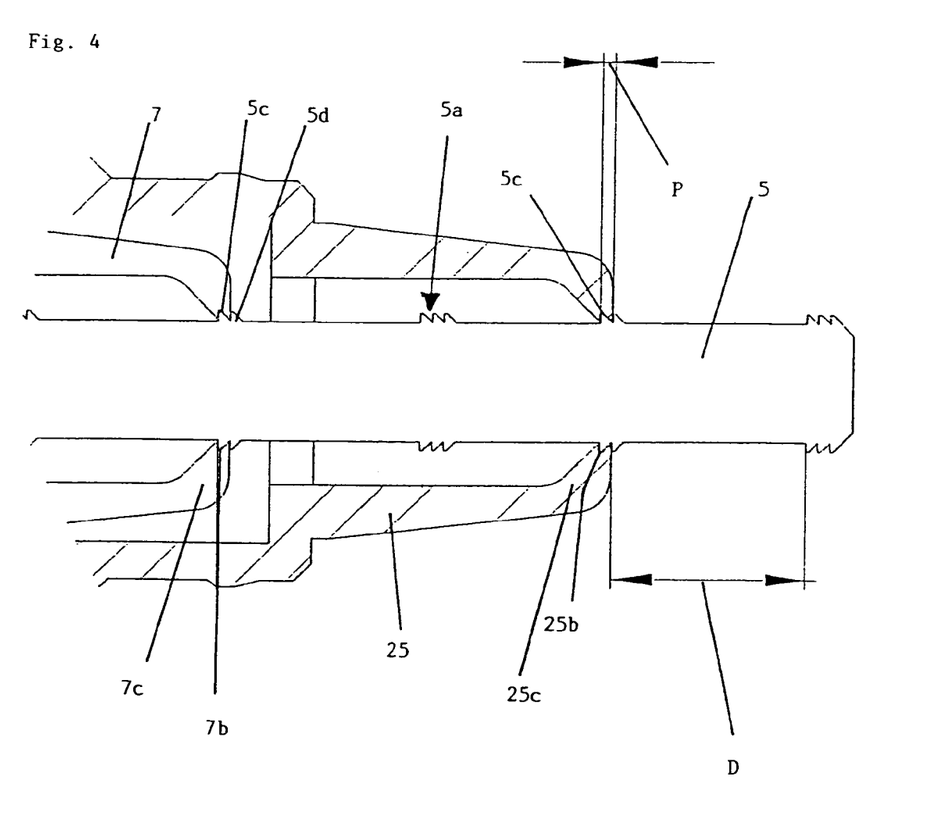
FIG. 4 is a representation corresponding to FIGS. 2 and 3, wherein a dosing has been carried out and a priming function is pending.

The toothed rod 5 displays several groups 5a of engagement elements 5b, 5c, 5d, which groups, in accordance with their function, display certain distances between them, which is made clear in FIG. 4. A front group 5a includes three teeth that are arranged in order to make possible a first de-aerating or priming after the placement of a new ampoule. Corresponding to this, a next-but-one group 5a of teeth is likewise formed with three teeth. The group 5a following the front group consists of two teeth and the group following the group 5a with three teeth again includes two teeth, which are sufficient for the administration both of a defined dose—front tooth 5d—and of a priming function. All of the following groups (not visible here) can then likewise have two teeth, in order to carry out both the dosed administration and the priming function. While teeth or tooth-like structures are depicted for the engagement elements, it should be appreciated that any suitable structure, integral with the toothed rod or attached thereto, may be used.

The advancing sleeve 7 includes two tooth-like jaws 7c that display respective engagement catches 7b that can be brought into engagement with the engagement elements or teeth, as the case may be, of the groups 5a of engagement elements. The teeth 5b to 5d are shaped such that with a forward movement of the toothed rod 5, the jaws 7c can be spread apart, the teeth having, in the advancing direction of the toothed rod 5 relative to the cylindrical axis of the cylindrical housing 1 (see FIG. 1) of the device, a flank that includes a rather acute angle with the cylinder axis of the housing 1 (see FIG. 1), which angle, for example, can be in the range of approximately 30 to 60°. Through this design, it is possible to allow the teeth 5b-5d to become disengaged from the catch 7b of the advancing sleeve.

In contrast, the rear flank, in the advancing direction, of each tooth of the toothed rod 5 is formed to be very steep, so that, opposite to the advancing direction of the toothed rod 5, the front end of the tooth-like jaw 7c, which is oriented perpendicular to the cylindrical axis of the housing, opposes a great resistance in the direction opposite to the advancing direction, so that a displacement of the toothed rod 5 opposite to the advancing direction is impossible or practically impossible.

The guide apparatus or guide sleeve 25 is designed with two tooth-like jaws 25c, similar to the advancing sleeve 7. The tooth-like jaws 25c display catches 25b that can be brought into engagement with the teeth 5b-5d in order to hold the toothed rod 5 in one position, while a pulling is performed on the advancing sleeve 7 by means of the dosing knob 9 in order to bring the advancing sleeve 7 out of engagement with the current tooth, in order to place the device according to the invention in a different operating state.

The guide sleeve 25 displays a stop 25a against which a corresponding stop 7a (see FIG. 3) of the advancing sleeve hits in order to limit, in the advancing direction, the advancing movement of the advancing sleeve relative to the guide sleeve 25, whereby, correspondingly, an advancing movement of the toothed rod 5 is also limited.

In some embodiments, the present invention provides for a sequence of successive administration and priming procedures. A new ampoule 3 may be inserted into the housing 1. In order to then carry out a first de-aerating of the injection needle N, the catch 7b of the tooth-like jaw 7c becomes engaged with an engagement element of the group 5a having three teeth, reproduced already in the advanced position, and moves the toothed rod 5 forward in the axial direction as soon as the dosing knob is pressed in the direction of the cannula N (see FIG. 1). The third tooth from the front of the front group having three teeth becomes disengaged from the catch 25b on the front tooth-like jaw 25c of the guide sleeve 25 and hooks behind the rearward flank of the rearmost tooth of the frontmost group of teeth. The front end of the toothed rod 5 thus presses on the piston 4 and a first priming takes place, placing the device into a state of readiness. Subsequently, the dosing knob 9 is pulled. The dosing knob 9 is firmly connected to the advancing sleeve 7 and through the pulling backward of the dosing knob 9, the catch 7b at the front end of the advancing sleeve 7 becomes disengaged from the tooth with which it was previously engaged.

If a dosing procedure is carried out, the tooth-like jaws 7c are slipped, slide over or travel along a toothless shaft segment of the toothed rod 5 between groups of teeth, in order to then become engaged with a following tooth of a following group. In this situation, the dosing knob is then completely pulled out and, through the pressing of the dosing knob 9 in the direction of the injection needle N, the piston 4 can be moved forward within the ampoule 3 in order to cause the administration of a predetermined dose of the injectable product.

If, with the next actuation, the dosing knob 9 is pulled back again, then the advancing sleeve 7 is also moved back and slips over the oblique flank of the following tooth of the toothed rod 5, a tooth 5c of a corresponding group 5a of teeth. If the dosing knob is further pulled, the advancing sleeve slips over the toothless region of the toothed rod 5, but within the range of its grasp cannot reach a following tooth of a following group. If the dosing knob is then depressed, the tooth-like jaws 7c slip back over the toothless region of the toothed rod 5 and then hook behind a steep flank of a tooth, in order to subsequently be able to perform a priming function if merely an advancing over a short distance takes place.

The tooth-like jaws 25c, 7c are radially flexible and are radially moved when the dosing knob and, through this, the advancing sleeve, are pulled, wherein the catch 7b, 25b slip over the associated teeth of the toothed rod 5 in each case. Subsequently, the respective tooth-like jaws return to their initial radial positions.

Subsequently, the above-described actions repeat themselves, the first priming of course taking place after the insertion of a new ampoule.

In FIG. 4, the dosing distance D between successive groups of teeth is explicitly represented. Equally so, the priming distance P between successive teeth of a group of teeth is shown. It should be appreciated that the dosing distance is substantially longer than the priming distance.

Figures 5, 5A:
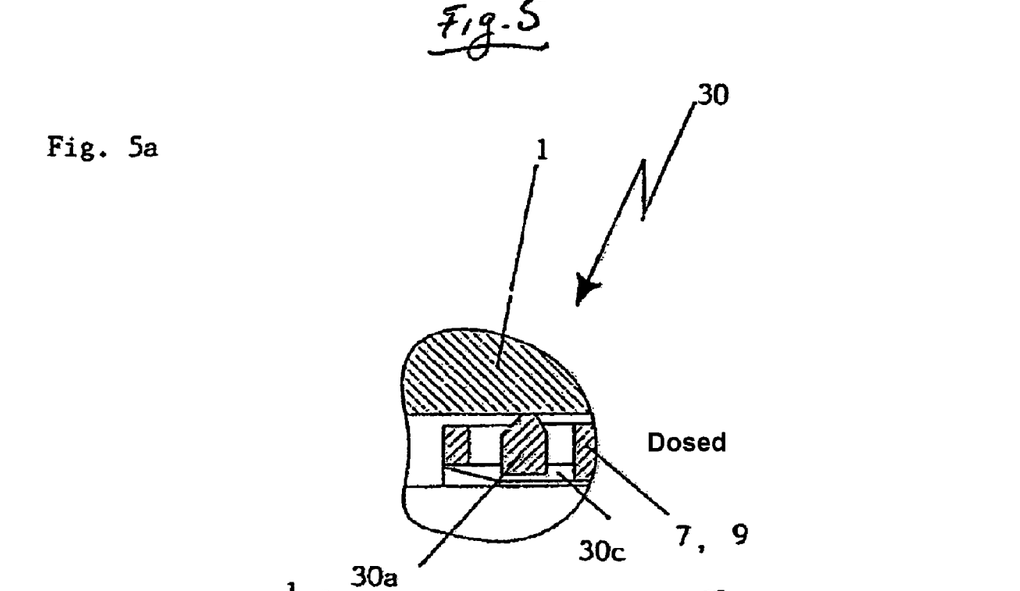
Figure 5B:
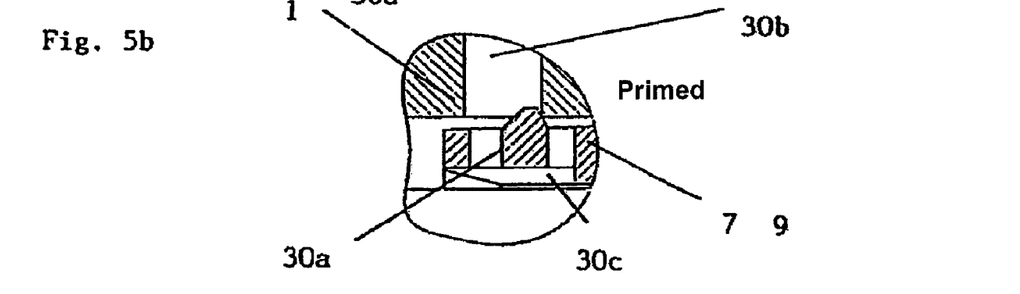
Figure 5C:
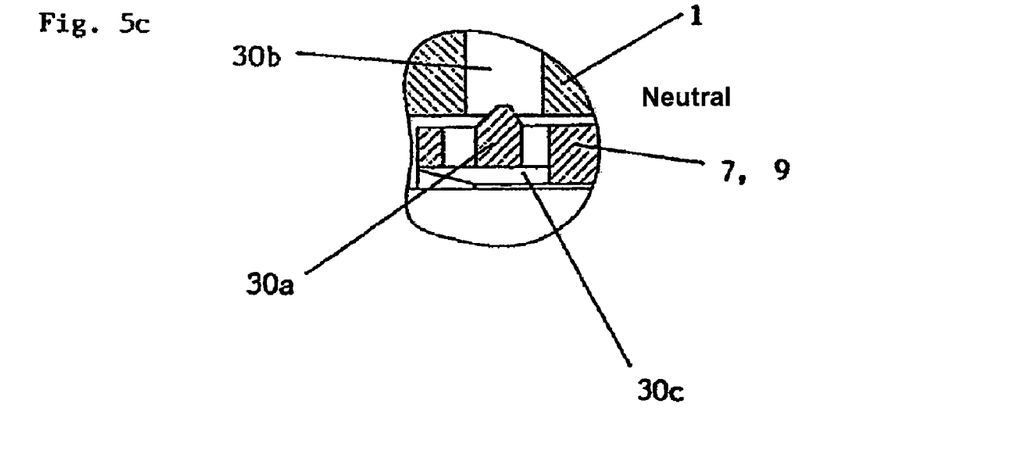

FIGS. 5a-5c show the priming indicator 30 in detail. In a dosing device according to the present invention in the dosed state according to FIG. 5a, a priming-indicator lobe 30a rests against the wall of the housing 1 and, thus, cannot be seen from the outside. A leaf spring 30c presses the indicator lobe 30a in the direction of the wall of the housing 1. The leaf spring 30c is attached to a lower section of the dosing knob 9 or the advancing sleeve 7. If now the dosing knob 9 is pulled, the indicator lobe 30a can slip into an indicator slot in the wall of the housing 1 and is then perceivable from the outside. This position is intended to indicate that the device is ready for a priming procedure and a priming is to be carried out.

In FIG. 5c, a "null" position is shown, in which the indicator lobe 30a indicates a neutral position of the device.

Thus, according to the present invention, a dosing or injection device is made available wherein the priming process is made easier for the user, i.e., the patient. The user is merely instructed to carry out the appropriate functions successively and, if a priming is to be performed, to undertake no injection, and vice versa.

In the foregoing description, embodiments of the present invention, including preferred embodiments, have been presented for the purpose of illustration and description. They are not intended to be exhaustive or to limit the invention to the precise forms and steps disclosed. Modifications or variations are possible in light of the teachings herein, and all such modifications and variations are within the scope of the invention as determined by the appended claims.

The invention claimed is:

1. A device for the dosed administration of an injectable product, comprising:
   a housing with a receptacle for the product;
   a drive mechanism movable via a dosing element supported displaceably in the housing, wherein the drive mechanism comprises engagement elements situated together in groups, each group comprising two or more engagement elements, a distance between the groups in a longitudinal direction corresponding to a maximum dosing amount of the injectable product and a distance between the engagement elements in the longitudinal direction corresponding to a priming amount of the injectable product, wherein the distance between engagement elements within the groups is substantially the same as the distance between engagement elements for each of the other groups; wherein the distance between groups is greater than the distance between engagement elements, and wherein the area on the drive mechanism between the groups comprises a circumferentially smooth area; and wherein
   the dosing element comprises an advancing sleeve displaceably supported in the housing and a dosing knob, the advancing sleeve coupled to the drive mechanism and to the dosing knob, said advancing sleeve configured to engage and disengage with the engaging elements and to transfer a propulsion force from the dosing knob to the drive mechanism, wherein the dosing knob moves the advancing sleeve in the longitudinal direction into and out of engagement with the engaging elements, such that the advancing sleeve moves along the circumferentially smooth area of the drive mechanism by the maximum dosing amount when the dosing knob is moved into a dosing state, and wherein when in the dosing state, the advancing sleeve moves to set a selected dose such that the maximum dosing amount is reduced.

2. The device according to claim 1, wherein the dosing element is coupled to the drive mechanism so that the dosing element at one time interacts with a group of engagement elements to administer the dosing amount and at another time interacts with an engagement element to release the priming amount.

3. The device according to claim 2, further comprising a priming indicator operably coupled to at least one of the drive mechanism and the dosing element for indicating a priming-function readiness.

4. A dosing device for the dosed administration of an injectable product, wherein the device comprises:
   a) a housing having a receptacle for the product,
   b) a conveying means for conveying the dose of the product to be administered,
   c) a drive means for the conveying means, the drive means comprising engagement elements, wherein the engagement elements are situated together in groups, each group comprising two or more engagement elements, wherein a dosing distance between the groups in a longitudinal direction corresponds to a maximum dosing amount of the injectable product and a priming distance between the engagement elements of a group in the longitudinal direction corresponds to a priming amount of the injectable product, and wherein the area on the drive means between the groups comprises a circumferentially smooth area; and
   d) a dosing element comprising an advancing sleeve displaceably supported in the housing and a dosing knob, the advancing sleeve coupled to the drive means and to the dosing knob, said advancing sleeve configured to engage and disengage with the engaging elements and to transfer a propulsion force from the dosing knob to the drive means, wherein the dosing knob moves the advancing sleeve in the longitudinal direction out of engagement with the engaging elements, such that the advancing sleeve moves along the circumferentially smooth area of the drive means by the maximum dosing amount when the dosing element is moved into a dosing state, and wherein when in the dosing state, the advancing sleeve is movable to set a selected dose such that the maximum dosing amount is reduced.

5. The dosing device according to claim 4, wherein the dosing element advancing sleeve comes into interaction with a group of engagement elements and, at another time, with an engagement element of a group, in order to administer a dosing amount the one time and to release a priming amount the other time.

6. The dosing device according to claim 4, wherein the advancing sleeve transfers a drive force from the dosing knob to the drive means.

7. The dosing device according to claim 4, further comprising a priming indicator, which signals an actuation of at least one of the drive means when the dosing knob has brought about a priming-function readiness.

8. The dosing device according to claim 7, wherein the priming indicator is actuated by a displacement element.

9. The dosing device according to claim 7, wherein the priming indicator is actuated by a displacement element comprising the advancing sleeve, said advancing sleeve mechanically coupled to the priming indicator.

10. The dosing device according to claim 4, further comprising a guide apparatus for holding the drive means in a position into which the drive means has been displaced by an advancing movement.

11. The dosing device according to claim 4, wherein equal distances are arranged between some of the groups in order to be able to administer equal dose amounts.

12. The dosing device according to claim 4, the smooth area having no engagement elements belonging to the groups.

13. A dosing device for the dosed administration of an injectable product, wherein the device comprises:
   a housing having a receptacle for the product,
   a conveying member for conveying the dose of the product to be administered,
   a drive mechanism for the conveying member, the drive mechanism comprising engagement elements, wherein the engagement elements are situated together in groups, each group comprising two or more engagement elements, wherein a dosing distance between groups in a longitudinal direction corresponds to a maximum dosing amount of the injectable product and a priming distance between the engagement elements of a group in the longitudinal direction corresponds to a priming amount of the injectable product, wherein the distance between engagement elements within the groups is substantially the same as the distance between engagement elements within each of the other groups; wherein the distance between groups is greater than the distance between engagement elements, and wherein the area on the drive mechanism between the groups comprises a circumferentially smooth area, the circumferentially smooth area having no engagement elements belonging to the groups; and
   a dosing element coupled to the drive mechanism, said dosing element comprising an advancing sleeve displaceably supported in the housing, said advancing sleeve engages and disengages with the engaging elements and transfers a propulsion force to the drive mechanism, wherein when the advancing sleeve is in a dosing state, the advancing sleeve moves in the longitudinal direction to set a selected dose such that the maximum dosing amount is reduced, wherein the dosing element is coupled to the drive mechanism such that the dosing element at one time interacts with an engagement element of a first group to release the dosing amount and at another time interacts with another engagement element within the first group to release the priming amount, and wherein the dosing element may not interact with an adjacent group until the dosing amount and the priming amount are released.

14. The device of claim 1, wherein the dosing knob moves into the dosing state by an axial movement in a direction opposite to an expelling direction, and the advancing sleeve is carried by the dosing knob and engages with an engagement element of a following group of engagement elements of the drive mechanism.

15. The device of claim 14, further comprising a guide sleeve coupled to the drive mechanism, wherein the guide sleeve engages with engagement elements of the drive mechanism and holds the drive mechanism in place when the advancing sleeve is carried by the dosing knob in the direction opposite to the expelling direction.

16. The device of claim 15, wherein the guide sleeve is positionable relative to the advancing sleeve to affect dosing.

17. The dosing device of claim 4, wherein the dosing knob is configured to move into the dosing state by an axial movement in a direction opposite to an expelling direction, and the advancing sleeve is carried by the dosing knob and engages with an engagement element of a following group of engagement elements of the drive means.

18. The dosing device of claim 17, further comprising a guide sleeve coupled to the drive means, wherein the guide sleeve engages with engagement elements of the drive means and holds the drive means in place when the advancing sleeve is carried by the dosing knob in the direction opposite to the expelling direction.

19. The device of claim 18, wherein the guide sleeve is positionable relative to the advancing sleeve to affect dosing.

* * * * *